(12) United States Patent
Hameed et al.

(10) Patent No.: US 9,198,712 B1
(45) Date of Patent: Dec. 1, 2015

(54) MINIGENERATOR

(71) Applicant: Chest Innovations, Inc., Pleasanton, CA (US)

(72) Inventors: Salmaan Hameed, San Jose, CA (US); Christopher Kilgus, Felton, CA (US); Moshe Zilversmit, Palo Alto, CA (US)

(73) Assignee: Chest Innovations, Pleasanton, CA (US)

( * ) Notice: Subject to any disclaimer, the term of this patent is extended or adjusted under 35 U.S.C. 154(b) by 0 days.

(21) Appl. No.: 13/919,446

(22) Filed: Jun. 17, 2013

Related U.S. Application Data

(63) Continuation-in-part of application No. 12/696,573, filed on Jan. 29, 2010, now Pat. No. 8,486,058.

(51) Int. Cl.
*A61B 18/12* (2006.01)
*A61B 18/00* (2006.01)

(52) U.S. Cl.
CPC ... *A61B 18/1206* (2013.01); *A61B 2018/00642* (2013.01); *A61B 2018/00696* (2013.01); *A61B 2018/00702* (2013.01); *A61B 2018/00732* (2013.01)

(58) Field of Classification Search
CPC .............. A61B 18/12; A61B 18/1206; A61B 18/1402; A61B 2018/0066; A61B 2018/1286; A61B 2018/1226; A61B 2018/00702; A61B 2018/0072; A61B 2018/00732; A61B 2018/00767; A61B 2018/00827; A61B 2018/00892; H03K 3/354; H03K 17/6871

USPC ........................................................... 606/34
See application file for complete search history.

(56) References Cited

U.S. PATENT DOCUMENTS

| | | | | |
|---|---|---|---|---|
| 4,034,762 A | * | 7/1977 | Cosens et al. | 606/40 |
| 4,126,137 A | * | 11/1978 | Archibald | 606/38 |
| 4,727,874 A | * | 3/1988 | Bowers et al. | 606/38 |
| 4,878,493 A | * | 11/1989 | Pasternak et al. | 607/99 |
| 5,370,645 A | * | 12/1994 | Klicek et al. | 606/35 |
| 5,540,681 A | * | 7/1996 | Strul et al. | 606/34 |
| 5,792,138 A | * | 8/1998 | Shipp | 606/38 |
| 6,023,638 A | * | 2/2000 | Swanson | 600/510 |
| 6,039,734 A | * | 3/2000 | Goble | 606/41 |
| 6,238,387 B1 | * | 5/2001 | Miller, III | 606/34 |

* cited by examiner

*Primary Examiner* — Michael Peffley
*Assistant Examiner* — Daniel Fowler

(57) ABSTRACT

The present invention provides an Electro Surgical Generator (ESG) optimized for lung biopsy. The ESG is exclusively battery operated and fits within the handpiece of modern endoscopic electrosurgical/electrocautery instruments, thereby avoiding wires, adapters, and coupling mechanisms. The ESG is adaptable to generate different waveforms that vary with respect to frequency, pulse width, amplitude, etc. through the use of timing circuits and voltage control (i.e. transformers). The ESG is both energy-efficient and safe. A closed loop feedback system featuring a monitor and controller ensure no more power than necessary is provided to achieve a goal current level. Dynamic Power Control (DPC) and Dynamic Temperature Control (DTC) systems vary power to maintain temperature with the lowest possible power. These features prolong battery life and guard against tissue damage. The generator includes other safety features such as resiliency against and the ability to overcome single fault events such as short circuits.

11 Claims, 4 Drawing Sheets

MINIGENERATOR

CROSS-REFERENCE TO RELATED APPLICATIONS

This application is a continuation of Ser. No. 12/696,573, filed Jan. 29, 2010, now allowed, the application being incorporated herein in its entirety by reference.

BACKGROUND OF THE INVENTION

1. Field of the Invention

The present invention relates to means for powering electrosurgical and electrocautery tools and instruments. More specifically, the present invention relates to cordless battery-powered means for generating power that are compact enough to fit within a handpiece, powerful enough for use in sealing and resecting operations in the lungs, and safe enough to provide risk reduction incentives over conventional generator systems. Most specifically, the present invention focuses on the aspects of the electrical circuitry design for the minigenerator system to provide increased energy efficiency, feedback and alert systems, and adjustable performance parameters to tailor the procedure to the needs of each patient.

2. Description of the Related Art

Battery-operated power generators are desirable for electrosurgical/electrocautery instruments because they eliminate the need for wires running from the instrument to generator boxes or wall outlets. This eliminates any chance of a leakage current fault that could harm the patient. That makes the unit inherently safe. In addition, safety compliance should be easy to obtain by sound electrical circuitry design that complies with well known and readily available industry standards (i.e. IEC 60601 and ISO 14971). With no wires, the surgeon would be free to articulate the unit without encumbrances, enabling more natural surgical techniques and a greater variety of techniques.

There have been other attempts to overcome the reliance upon electrical wires and cords in providing electrosurgical/electrocautery tools with a reliable power supply. These attempts have confronted the dilemma in that eliminating the wall outlet electrical power source and relying completely on battery power typically makes the instrument so bulky that it is no less awkward to use than instruments attached to wires. Alternatively, providing a smaller battery to make the instrument easier to handle may be okay for more refined smaller scale surgical work but current circuitry designs and modes of usage cannot provide the amount of power necessary for more intensive surgeries in larger organs. Accordingly, several designs have accepted wires as necessary for the supply of a sufficient amount of power. These designs have focused on alternatives that reduce the negative aspects of wires (i.e. the ability of wires to get in a surgeon's way) rather than eliminating them altogether. Examples follow.

U.S. Pat. No. 6,039,734 (hereinafter USP '734) entitled "Electrosurgical hand-held battery-operated instrument" by Colin Charles Owen Goble and assigned to Gyrus Medical Limited (Cardiff, GB) discloses an instrument that is truly without wires. However, it is noted that "[t]his instrument is primarily, but not exclusively, intended for fine surgical work, such as spinal, neurological, plastic, ear-nose-and-throat and dental surgery, and office procedures." There is no mention of lung, pleural, chest, or thoracic capabilities. Additionally, the instrument uses a single treatment electrode and is monopolar (see Abstract, claim 1, 1:29-31, etc.). The array of surgical procedures compatible with such a design is limited. The minigenerator of the present invention can be used with bipolar instruments having multiple treatment electrodes and this expands the potential applications. Since the battery-operated instrument of USP '734 is monopolar it requires a return path to be built into the housing of the instrument in order to avoid localizing current in a patient's tissue in the region of a return pad. The return path takes the form of an electrically conductive shield outside the generator that provides capacitive coupling between the generator and its surroundings (see Abstract, claims 7-9, 1:38-43, etc.). This built-in return path adds some bulk to the device as the layering is: generator—insulator—conductive shield—insulator. This generator also uses and provides a conductive path of alternating current (AC) (see claim 18). The minigenerator of the present invention can also provide direct current (DC) for electrocautery in which current does not enter the patient's body. Direct current electrocautery may be safer in some situations.

U.S. Pat. No. 5,961,514 (hereinafter USP '514) entitled "Cordless electrosurgical instrument" by Gary L. Long, et al. and assigned to Ethicon Endo-Surgery, Inc. (Cincinnati, Ohio) achieves a "cordless" electrosurgical instrument in a narrow sense of the term in that the instrument itself is, in fact, cordless but for power it is required to screw-in or plug-in to a trocar adapter unit that has wires and is itself electrically charged by a wall outlet. The outside of the tubular instrument has electrical contacts that receive energy as the instrument is passed through a trocar cannula. Thus, the instrument must be passed through and in contact with the trocar cannula to receive energy and the trocar adapter unit has wires. Connecting the instrument to the trocar adapter provides an extra step and obligation for a surgeon to perform before beginning to operate. Requiring the instrument to pass through a trocar cannula limits the angles and directions in which an instrument can be manipulated to access and treat a target site since it has to pass through the wired trocar adapter first. Thus, the advances of this system, if any, seem marginal. Typical voltages coming from a wall electrical outlet are much higher than the maximum voltages of reasonably-sized batteries and passing such a high voltage through a trocar cannula adapter unit in proximity to the patient could be dangerous.

U.S. Pat. No. 6,569,163 (hereinafter USP '163) entitled "Wireless electrosurgical adapter unit and methods thereof" by Cary Hata, et al. and assigned to Quantumcor, Inc. (Irvine, Calif.) improves upon the wired trocar cannula adapter unit of USP '514 by providing an adapter unit that "contactably couples" to an energy source upon direct physical contact by the surgeon (4:30-38). "Contactable coupling" is defined in the patent as "coupling two electrical contact elements by contacting without plugging or connection" (4:27-30). However, the system is not truly wireless in that wires exist, it is just that they are divided into separate discrete segments, hidden, and insulated. Wires extend through a surgeon's glove and/or gown to terminate in at least one electrically conductive patch zone (or two patch zones for bipolar instruments) that provides power to the adapter unit upon direct physical contact. A drawback of this system is that the instrument itself does not contactably couple to the power supply. Rather, the wireless adapter unit (WAU) stands between the electrical source in the surgeon's glove or gown and the electrosurgical instrument to be powered. The instrument itself actually connects to the WAU with a cable cord 25 and receptacle 24 (see FIG. 4) or it connects through wires stripped of their insulation and a spring-loaded plug (5:31-41). It seems it would be a better design to eliminate the adapter unit and contactably couple the electrical system in the surgeon's glove/gown directly with the instrument to be powered. This would streamline the connections and eliminate the duty to line-up and connect components in situ. This drawback is discussed and compared to the prior art (see 5:23-28, 5:31-41, and FIGS. 4A and 4B). USP '163 teaches away from a battery pack by suggesting the contactable coupling means described therein is superior because it doesn't take up space while batteries do and can make an instrument bulkier and heavier (2:7-14 and 4:36-38).

The minigenerator power system of the present invention overcomes the issues of all of these references by providing a truly wireless system that avoids both a separate adapter unit and the need for a coupling mechanism and is capable of being used with bipolar (in addition to monopolar) instruments. The elimination of a coupling mechanism reduces instrumentation set-up time and the on-site power generation source reduces charging or power-up time. The special handpiece is hermetically sealed, without any external wires, and with a modern battery having specially designed circuitry that minimizes power usage for a lighter, longer-lasting battery-powered instrument.

BRIEF SUMMARY OF THE INVENTION

The present invention provides an electrosurgical/electrocautery generator that is completely cordless, free of adapters, and entirely battery-powered. The generator is compact enough to fit within a handpiece of an electrosurgical/electrocautery instrument without adding weight or bulk. The generator is designed to fit within the handpieces of modern, smaller, endoscopic surgical instruments. The battery component of the generator can be as small as contemporary cell phone batteries (i.e. around 1.5"×1.5"×0.25").

The cordless nature of the entirely battery-powered generator provides safety improvements for both the patient and healthcare providers (surgeon and operating room staff). There are no cords for anyone to trip over and there is no risk of frayed wires or leaking voltage from poorly insulated or worn wires. The electric circuitry of the generator of the present invention has also been specially designed to perform at reduced voltage levels. The system can run off of a battery in the range of 6 volts to 24 volts and all voltage levels in the circuitry are low, at battery level, until the very last transformer (see last transformer T2 in FIG. 2 final output diagram). Conventional generators with wires that rely on electrical energy from wall outlets typically work with 100-250 volts (V) alternating current (AC). Thus, the present design reduces widespread higher voltages.

Other advantages of the cordless battery-powered design of the generator are that it is much more portable. Physicians working out of several hospitals, clinics, and out-patient offices (as many do) can carry the same preferred instrument with them from place to place, thereby building skill and confidence from using the same piece of equipment. Generator portability also reduces the need for a separate instrument and generator at every site or on every floor of a facility, thereby reducing overhead expense which is passed along to maintain lower procedure costs for patients and insurance companies. The generator system is so small compared to conventional plug-in wall units it is even easy to travel with including by plane transportation. Surgeons should prefer this cordless battery-powered generator because it drastically increases their safe range of motion during surgery, giving them greater ability to "dance" about the operating room and flex/bend/turn as necessary to obtain the best treatment angles without worrying about tripping on wires, getting cords tangled, or traversing the patient with electrically charged cords. Greater instrument controllability results in more precise and accurate cutting (more hit, less miss when aiming at a target) which consequently results in less bleeding from hitting unintended vessels and other structures. In addition to less bleeding, there is less structural damage to unintended structures. Better maneuverability also enables improved linear cutting with less deviation from a path along a line.

The minigenerator of the present invention is ideal for powering many types of electrosurgical/electrocautery instruments. The minigenerator can be used universally with any electrosurgical/electrocautery tools so long as it can fit in the handpiece of the instrument used to power those tools. Exemplary tools the minigenerator can be used to power include those with electrodes, optical fibers, barbs, blades, scissors, jaws, tissue-contacting surfaces, vibrators, heaters, ablators, ultrasonic generators, mechanical cutters/corers, spinning cutters, etc. It is especially well-suited for powering instruments that cut and seal tissue, including those that cut and seal through non-mechanical energy transfer means such as radiofrequency ablation, tissue welding, cauterization, infrared lasers, etc.

The electronic circuitry of the generator is arranged in an interconnected closed loop functional feedback system such that power drained from the battery and converted by the converter can be adjusted as necessary to maintain a desired level of current or power supply to the final output. This internal system can also be connected with another external component that monitors an external variable, in a patient's body, that is impacted by the final output current or power. For example, a thermocouple might be used to monitor the temperature of a site in a patient's body. The temperature of a site in contact with the electrosurgical instrument is influenced by the power provided by the battery and the current provided to the final output. By providing Dynamic Temperature Control (DTC) and Dynamic Power Control (DPC) the present invention stabilizes the temperature at an optimal level (or range) while using the minimum amount of power necessary. Resistance is another variable that can be measured by a sensor to monitor the condition of the tissue to ensure it stays within safe ranges while providing the best therapeutic benefit.

This feedback system saves energy by providing no more energy than is necessary to maintain a given level of current or power to the final output or to maintain the value of a variable that measures a characteristic of tissue in a patient's body at a desired therapeutic level. The hydrated condition of live tissues in a patient's body allows them to conduct electricity and permits a reduction in power necessary for effective treatment compared to desiccated tissues with little or no conduction. However, the extent of hydration and the resistance of tissues changes over the course of treatment and can change abruptly. These changes impact the power requirements to achieve the same effects. Continual feedback provides for the necessary power adjustments to maintain constant therapeutic benefits and avoid dangerous extremes that could cause unwanted outcomes including charring. A more energy-efficient instrument also provides an economic benefit by reducing power costs.

According to a preferred embodiment, the generator also includes a means for tailoring the frequency, pulse width, and amplitude of the waveforms generated to match the needs of each patient and procedure. Timing circuits in the controller can be used to control the frequency and pulse width while the amplitude is directed by varying the voltage to the final output stage.

The basic requirements for the circuit are a closed conductive path and an energy source. The battery described herein provides the energy source. The design of the electrosurgical/electrocautery instrument that connects the battery to the specific tools and elements it powers provides the closed conductive path. Other standard circuit elements can be added to obtain the desired functionality, feedback, controllability, and safety features. These elements include: capacitors, resistors, transistors, transformers, inverters, antennas, diodes, etc. A capacitor stores electric charge. A capacitor is used with a resistor in a timing circuit. It can also be used as a filter, to block DC signals but pass AC signals. A resistor restricts the flow of current, for example to limit the current passing through a light emitting diode (LED). A resistor is used with a capacitor in a timing circuit. A transistor amplifies current. It can be used with other components to make an amplifier or switching circuit. A transformer comprises two coils of wire linked by an iron core. Transformers are used to step up (increase) and step down (decrease) alternating current (AC) voltages. Energy is transferred between the coils by the magnetic field in the core and there is no electrical connection between the coils. An inverter can have only one input and the output is the inverse (opposite) of the input (i.e. the output is true when the input is false). An inverter is also called a "NOT gate". An antenna receives and transmits signals, typically radiofrequency (RF) signals. A diode is a device which only allows current to flow in one direction.

Advantages of the invention will be set forth in the description and drawings which follow, and in part will be obvious and implied from the description and drawings, or may be learned by practice of the invention. Advantages of the invention may be realized and obtained by means of the instrumentalities and combinations particularly pointed out hereinafter and any other means suggested by them.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 2:
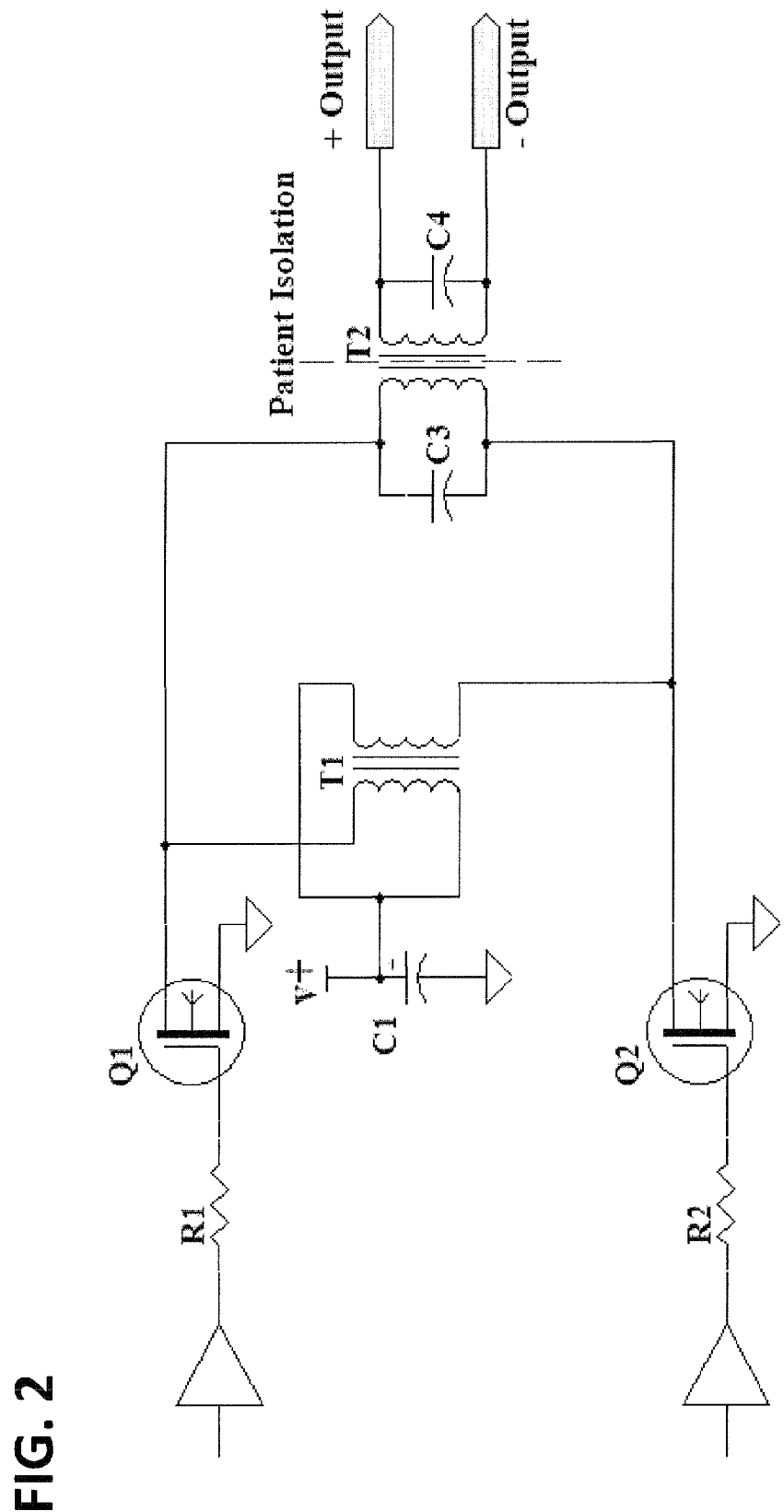
FIG. 2 shows a circuit diagram demonstrating the final output and how this is fed by and isolated from the power generation components and remaining circuitry.
Figure 3:
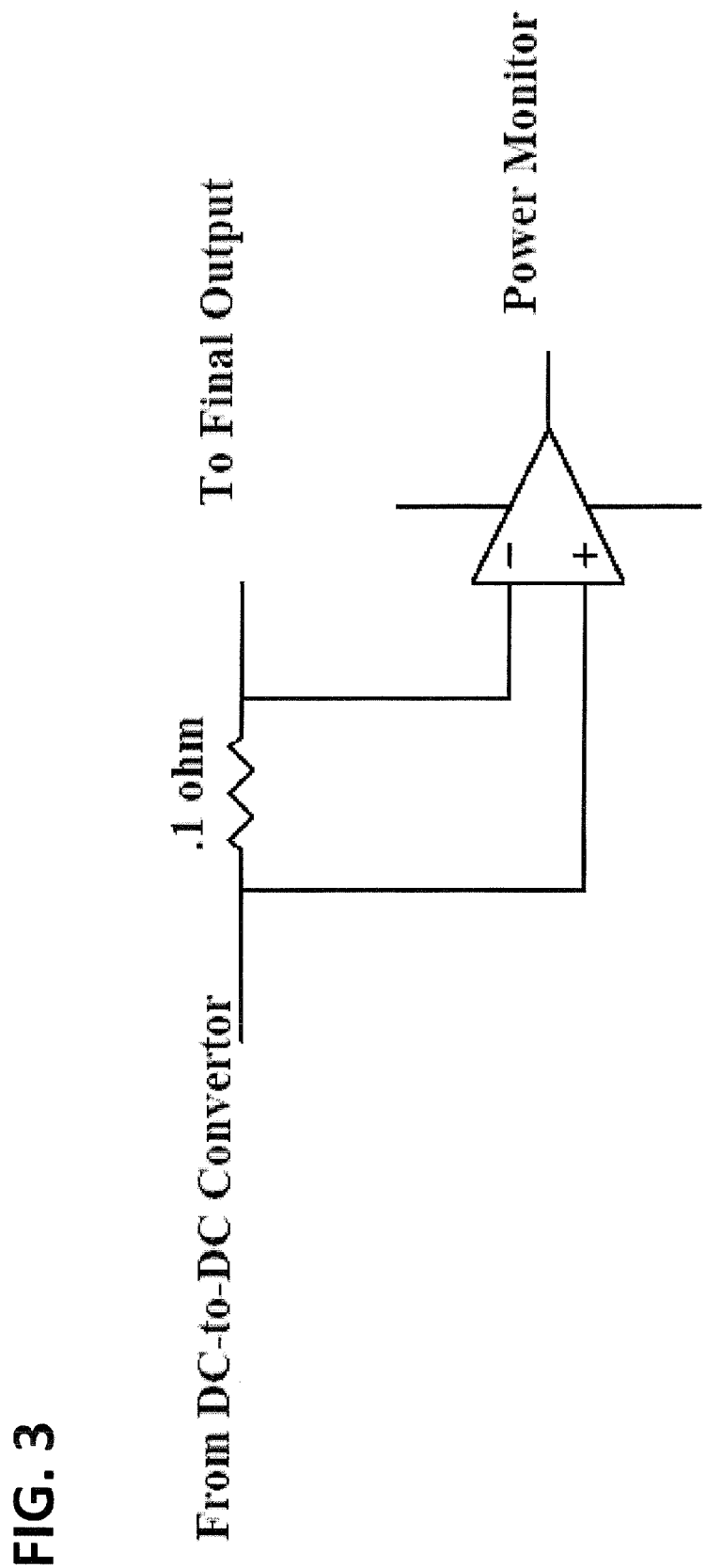
FIG. 3 shows a power monitor that is used to sample the current by developing a voltage drop across a small resistance of 0.1 ohm. The voltage is numerically equal to the amperage drawn by the final output stage divided by 10. The voltage value is fed to the controller to determine if it is within an acceptable range.

The design has been optimized for safe, energy-efficient battery operation. All voltage levels in the circuitry are low, at battery level, until the very last transformer T2 (see the final output diagram shown in FIG. 2 illustrating how the last transformer T2 is isolated). The last transformer multiplies the voltage and isolates the patient from the entire circuit. The output stage is simple, but efficient, ideal for battery operation. The use of a "swinging choke" T1 (see FIG. 2) provides the necessary positive and negative outputs by using only two Field Effect Transistors (FETs).

Using a wide range input DC-to-DC converter design, the latest battery technology can be utilized. Any battery input from about 6 volts up to 24 volts can be accommodated. The output of the DC-to-DC converter does not vary with changes in the input. Therefore the unit can provide an energy output (i.e. radiofrequency or RF output) that is independent of battery voltage. This fixed output feature makes battery life deterministic and predictable. A radiofrequency output is listed as exemplary only and is not limiting. The generator of the present invention could also be used in the handpiece of instruments that produce other energy forms as outputs, including infrared (IR), ultraviolet (UV), ultrasonic, lasers, etc.

A battery can be selected to easily provide enough power for the procedure, plus a large safety factor, and still fit comfortably in the handle of an electrosurgical/electrocautery instrument. Typical power requirements for a lung biopsy are 30 watts for 30 seconds. Using two 12-volt batteries with only 50% conversion efficiency, the battery capacity requirement would be 0.04 Amp-Hr:

30 W=12V @2.5 A, 2.5 A×0.5 min×Hr/60 min×2 (50% efficiency)=0.04 Amp-Hr.

Small lithium-ion batteries in a portable form factor typically provide 0.5 Amp-Hr. This provides an excess capacity of greater than ten times (10×): 0.5/0.04=12.5.

Monitoring the power supplied to the final amplifier stage and not supplying power if a momentary short circuit occurs, as happens in these procedures, extends battery life. During a short circuit the power required theoretically becomes infinite and battery life would be jeopardized if it were not detected. According to a preferred embodiment, the current to the final amplifier (final output) is monitored. This current is directly proportional to the amount of power (i.e. radiofrequency power) being supplied to the tissue. If a short occurs, the current detector will command the controller to cut the power, wait for a moment, then reapply a small amount of power to determine if the short has been cleared. If it has been cleared, then the full procedural power is restored. Alarms in the form of an audible sound (i.e. a beep or different pitches and tones), lights (including colored or flashing), and/or vibration (or another tactilely sensed change) are provided if a short circuit occurs so that the surgeon is immediately aware.

The power monitor samples the current by developing a voltage drop across a small resistance of 0.1 ohm. This voltage is numerically equal to the amperage drawn by the final output stage and divided by 10. The voltage is fed to the controller to determine if it is in an acceptable range. Due to their interrelationship, if the voltage is in the acceptable range the current (amperage) is also in the acceptable range.

The frequency, pulse width, and amplitude of the energy output (most commonly RF output for energy in the radiofrequency range) to the patient are all adjustable in real time. Handpiece and/or foot treadle controls can be provided so that the surgeon can adjust these parameters easily on-the-spot without interrupting cutting/resecting or sealing of tissue. Then, there is no need to stop, walk to a main console and manipulate controls there. Optionally, a programmer may also be incorporated and used when a particular waveform pattern is desired that can be too complicated or exhausting to achieve by manual operation (handpiece control buttons or foot treadle) alone. The ability to adjust the waveform characteristics allows the unit to produce the most effective waveform for each particular procedure. Different procedures, different instruments, different patients, and different sites on the same patient have different needs with respect to waveforms. The generator of the present invention is designed to accommodate all of these needs to achieve better surgical results with shorter procedures and longer battery life.

Figure 4:
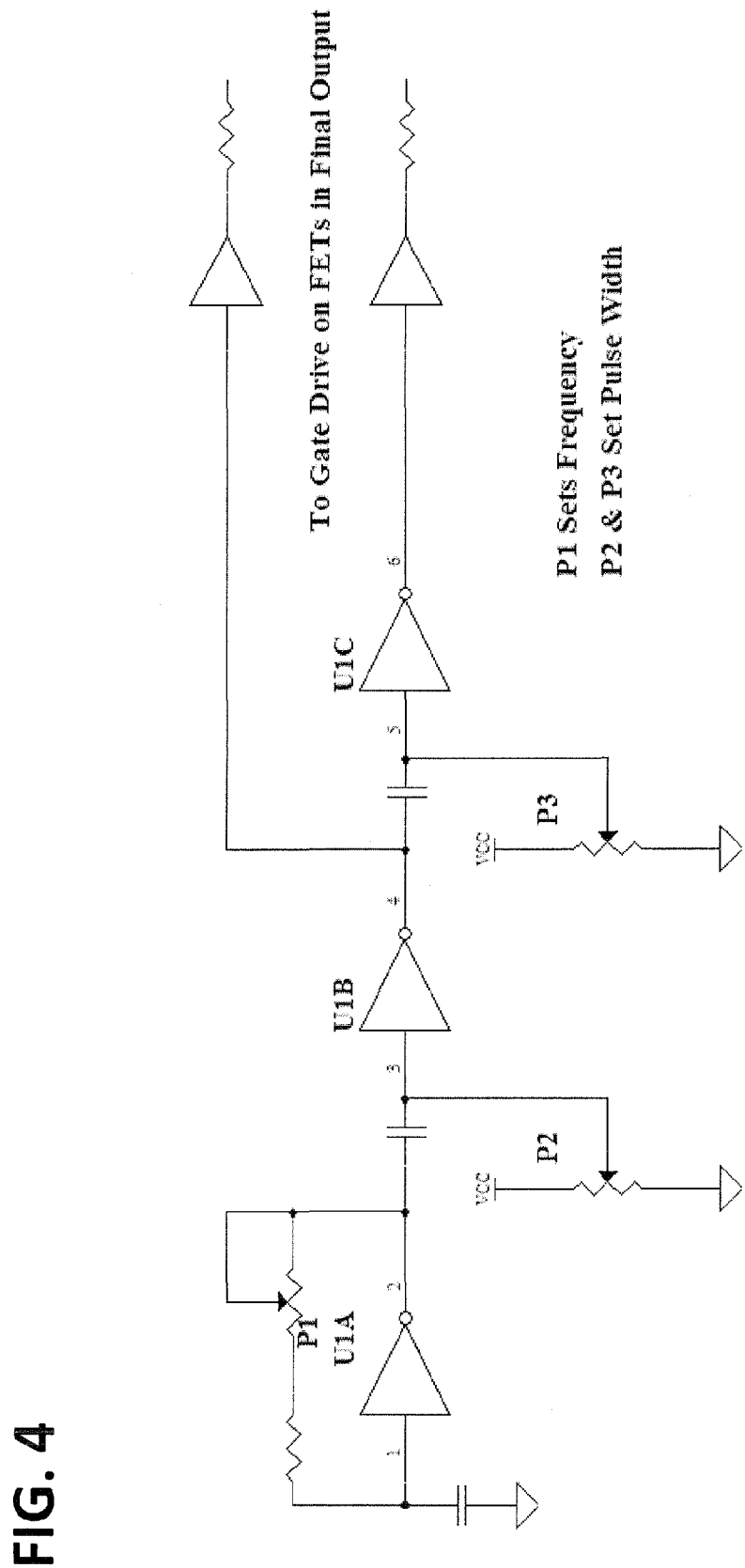
FIG. 4 shows a simple analog version of a timing circuit inside the controller used to generate the frequency and pulse width.

The frequency and pulse width are generated with timing circuits in the controller. The controller communicates with the current monitor and these variables can be adjusted, if desired, in response to changes in the current. The timing circuits can be analog or microprocessor circuits. A simple analog version of a proven circuit is shown in FIG. 4.

Figure 1:
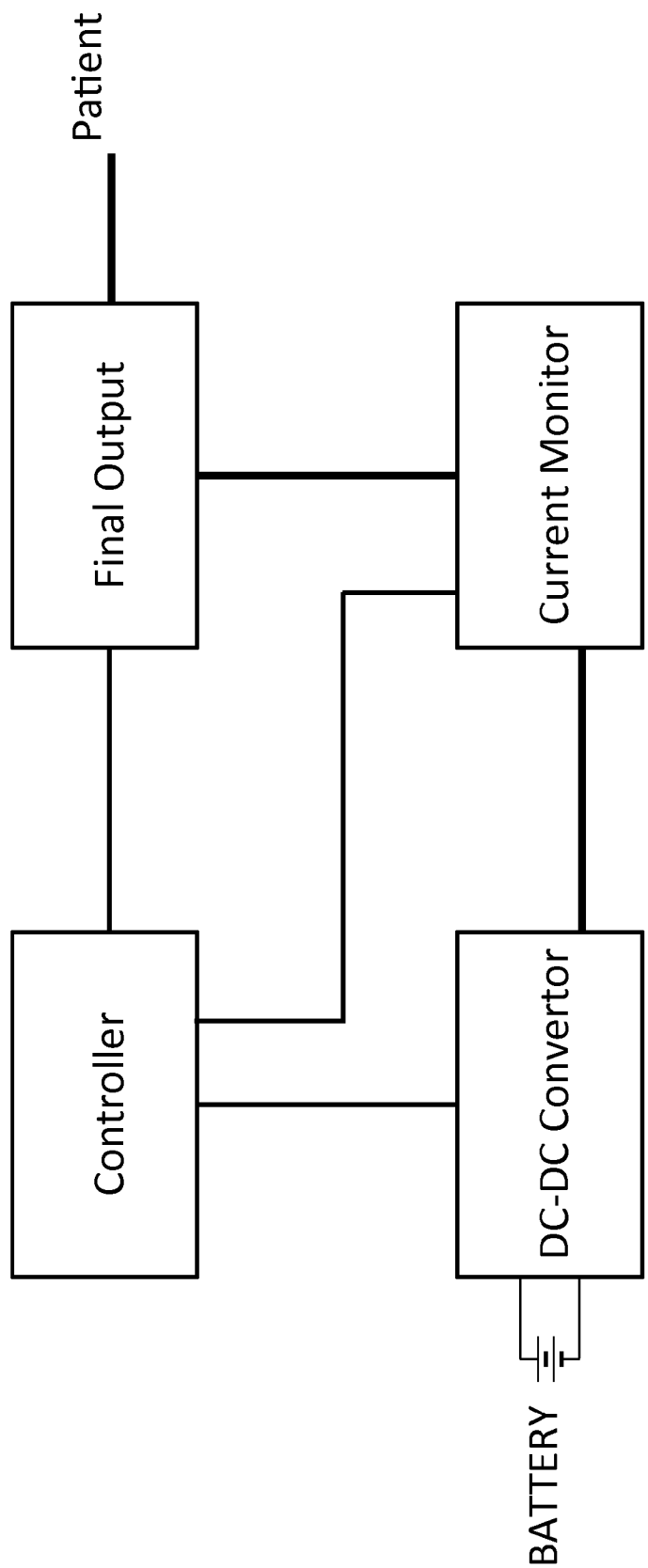
FIG. 1 shows a block diagram illustrating the basic feedback loop of the circuitry and showing how the current monitor and controller work together to adjust the amount of energy drained from the battery and/or processed by the converter and provided to the final output.

The amplitude is a function of the voltage to the final output stage. That voltage is determined by the set point on the DC-to-DC converter, which is, in turn, provided by the controller. As shown in FIG. 1, the controller communicates with the converter, the current monitor, and the final output to ensure the optimum voltage is provided to the final output from the converter. As previously stated, this voltage passed along to the final output is not dependent upon the voltage of the specific battery selected to power the generator. The voltage to the final output can be set at a specific value and that value can be achieved with any battery used by the generator.

Additional sensors can be provided near a distal tip of the electrosurgical/electrocautery instrument powered by the generator at a target site in a patient's body to measure these variables (frequency, pulse width, amplitude) to ensure the goal values are achieved and to detect the numerical values at which the best performance occurs. Performance can be felt by the surgeon manipulating the instrument, seen on a monitor for endoscopic procedures, or seen with direct vision for open procedures.

By utilizing temperature feedback (Dynamic Temperature Control or DTC) which can be determined from a thermocouple at the tissue site, power can be dynamically varied (Dynamic Power Control or DPC) during the procedure. It is possible to start the procedure at full power, monitor the temperature of the tissue, and reduce the power as soon as the temperature starts to approach the therapeutic temperature. A closed loop controller would provide just enough power to maintain the desired temperature and thereby maximize battery life. For example, temperature ranges of 60-75° C. in tissue have been shown to be optimal for cutting and sealing procedures (see Massachusetts Institute of Technology's Technology Review of Nov. 19, 2008: "Healing with Laser Heat—Surgical lasers could soon heal cuts as well as make incisions" by Lauren Gravitz.)

The circuitry of the system can vary among the different embodiments so long as the objective is satisfied: energy conservation while providing a desired effect on target tissue that dynamically responds to the changing state of tissue as it is heated. Accordingly, the effect on tissue can be made to approach a known optimal range as measured by one or more tissue characteristics including resistance, temperature, density, moisture content, etc. In some cases the desired effect is assured by maintaining constant temperature of the tissue as energy is transferred to it. As the material nature of the tissue changes as it is heated, the amount of energy supplied to the tissue to maintain the optimal temperature may change. Temperature measures the degree of heat in the tissue and an average kinetic energy of particles in the tissue.

According to a preferred embodiment, the circuitry comprises at least one capacitor and at least one resistor. More preferably, there are three capacitors and two resistors with a resistance of at least one resistor between 0.05 and 0.15 ohms. According to a preferred embodiment, there is a transformer that is a swinging choke transformer and there are two field effect transistors (FETs), such that the swinging choke transformer provides both a positive and a negative output, as necessary, by using only the two field effect transistors (FETs).

As for the power source and converter, preferably, the battery has a voltage from 6 volts up to 24 volts and the energy converter is capable of handling DC-to-DC (direct current to direct current) conversion.

The controller preferably includes at least one timing circuit. The timing circuit may be an analog or a microprocessor circuit and desirably has at least one inverter or NOT gate. To provide a desired effect on tissue the final output preferably operates at 30 watts or more for 30 seconds or longer.

The exact power level provided by the final output to tissue and the length of time it is provided over to produce the desired effect will depend upon the details of a particular patient. Feedback sensors in situ ensure the system is properly calibrated for each individual patient and that the appropriate amount of energy is transferred to the tissue to produce a desired sealing or resecting effect without charring, burning, etc. Independent feedback sensors of one or more types (including those that measure temperature, resistance, moisture content, etc.) can be positioned in a patient at a tissue site to which an electrosurgical/electrocautery instrument (powered by the minigenerator herein) is applied and these sensors can be connected to directly or wirelessly communicate with the controller of the minigenerator. In some cases the sensors are part of the distal end of the electrosurgical or electrocautery instrument with which the minigenerator is used while in other cases they are independent components separately embedded in the tissue.

Next, a general procedure for the collection of biopsy samples from a lung is outlined. The generator of the present invention could be used to power the electrosurgical instruments used to perform the biopsy procedure. However, this is just one application and is not intended to be limiting. The generator also can be used after biopsy to power more intensive treatment procedures with the objective of removing substantial quantities of tissue (much larger than the sizes needed for biopsy analysis) and sealing large regions (i.e. to reduce the spread of cancer or other disease, redirect flow, and/or prevent fluid accumulation or leakage).

Although there is an emphasis on the lung, the generator is not limited to powering procedures within the lung. One having ordinary skill in the art will recognize that the generator and methods described herein are readily adapted for the collection of biopsy samples, sealing (as a substitute for threaded sutures), and cutting/resecting operations in several regions of the body including nerve repair, blood vessel repair, cornea transplants, etc.

General Procedure

Step One: Consent, Anesthesia, Medical Staff, and Set-Up

Prior to beginning the procedure, the informed consent of the patient should be obtained.

One advantage of the present invention, as compared to traditional open-surgery biopsy techniques, is that it is done under local anesthesia rather than general anesthesia. Consequently, there is less interference with the homeostasis of bodily functions and recovery time is reduced permitting patients to avoid lengthy and expensive post-operative stays in the hospital recovery unit. Further, local anesthesia generally allows for a quicker post-operative assessment of the patient's condition and of the success of the procedure. The preferred drug of choice for local anesthesia in the present procedure is a long-acting local anesthetic agent like bupivacaine. Lidocaine, novocaine, ropivacaine and procaine may also be used. Intravenous sedatives including versed, morphine, fentanyl and other agents enhance the effects of the local anesthetic agent by causing the patient to become sleepier, less anxious, and number to sensations like pain. An anesthesiologist or anesthetist should be required to standby during the biopsy procedure until the operating physician is very comfortable in using the devices described herein.

This procedure is to be done in a procedure room, operative room, or in the ICU (Intensive Care Unit). A RN (Registered Nurse) should be positioned bedside throughout the procedure and sterile precautions should be used. A telemetry unit should be used to monitor heart rate and blood pressure as needed. Oxygen saturation should also be measured throughout the procedure.

Typical endoscopes provide channels for gas and fluid exchange between the external environment and the internal biopsy site. Carbon dioxide or an equivalent gas may be insufflated to the biopsy site through such a channel, during the biopsy procedure, at flow rates of 2-4 liters per minute. Carbon dioxide gas is preferable because it is non-combustible (unlike oxygen), dissolves in blood, and does not cause clots or bubbles when introduced into the rib-restricted thoracic cavity (unlike air). Any other gas having these same advantageous characteristics that is otherwise medically compliant and safe for introduction within the interior of the thoracic cavity may also be used.

The patient's diagnostic data is to be reviewed by a pulmonologist. It is preferable to have CXR (Chest X-Ray) and CT (Computed Tomography) scans readily available. Preferably, a thoracic surgeon on standby should be available for back-up support and assistance.

Step Two: Incision, Insertion of Minithoracoscope, and Insufflation to Induce Pneumothorax The point of entry is based on the diagnostic data as determined by the pulmonologist. Once the point of entry is determined, the operative site surrounding the point of entry is prepared and draped in a sterile manner.

Next, the local anesthetic agent is infiltrated. A total of 5 mL is usually adequate to anesthetize from the skin to the pleura. A needle is inserted into the intrapleural space. An ease in injection is noted as the needle tip enters the pleural space. This can be confirmed by aspirating air.

A blade knife (size: 11-gauge) is used to make an incision (approximately 2 mm). This incision will facilitate the entry of the Chest Innovations (trademark) (hereinafter, CI) minithoracoscope (trademark). The entry point is always superior to the rib to prevent injury to the intercostal vessels. The CI minithoracoscope has a multi-port minitrocar (trademark) that is held in the midportion of the scope for better directional control. Steady forward pressure is needed to enter the pleural space. Insufflating the internal region during the introduction of the minithoracoscope (or other instruments) is preferred to reduce the possibility of lung injury. Providing continuous insufflation to the internal region of the site to be biopsied also facilitates visualization and prevents fogging of the CI minithoracoscope.

As the pleural space is entered, there is a "give" or sudden drop in pressure, at which time the multi-port minitrocar is removed. Carbon dioxide insufflation continues into the intrapleural space at 2 liters per minute following the removal of the multi-port minitrocar to induce a pneumothorax causing the lung to collapse. When the lung is collapsed, it is easier to visualize, grasp, and manipulate for obtaining a biopsy. It is also easier to reach a greater number of target locations for sampling from a single incision site when the lung is collapsed. During the procedure the intrapleural pressure is maintained at less than 8 mmHg. The anesthesiologist or anesthetist keeps a watch over the blood pressure as excessive carbon dioxide insufflation may cause hypotension, such as from a mediastinal shift as pressure changes in the thoracic cavity push the heart over. In the event of hypotension, the situation can easily be corrected by stopping the flow of carbon dioxide and aspirating the port. Accordingly, it is important to use a low flow rate of carbon dioxide throughout the procedure to avoid rapid fluctuations in blood pressure and intrapleural pressure.

Step Three: Insertion of Camera and Instruments

As an alternative to relying solely upon the tactile sensation of a pressure drop to determine when the pleural space has been entered, a second option is to introduce a CI minithoracoscope with a camera in one of its ports so that insertion of the biopsy needle and insufflation of carbon dioxide are under direct vision. Using this option, the CI minicamera (trademark) is inserted through a port of the minithoracoscope. The location of the CI minithoracoscope within the interior of a patient can be confirmed by visual inspection of the external monitor which receives image signals transmitted by the minicamera. The monitor is usually available with most scope towers. The CI minicamera may need to be defogged occasionally throughout the procedure. Outside of the body, a solution such as "Fred" by Dexide, Inc. or "Dr. Fog" by O. R. Concepts, Inc. (see also U.S. Pat. No. 5,382,297 assigned to Merocel Corporation) can be used to defog the minicamera. Inside of the body, directing the source of carbon dioxide insufflation at the lens of the minicamera may assist to defog.

As the minithoracoscope advances internally through the prospective biopsy region, the pathology is identified and reviewed. Pictures are taken by the minicamera for documentation and correlation with biopsy samples.

Once a target biopsy region is identified based on the images transmitted by the minicamera, the working miniport (trademark) of the minithoracoscope is ready to be used. The miniport is an instrument channel or a fluid/gas exchange channel. The CI mininstruments (trademark), including forceps, staplers, and energy-transferring sealing and separating devices are inserted to obtain biopsy specimens. The specimens are then removed for pathology analysis and/or for culture and sensitivity studies. If bleeding is encountered during the internal manipulation of CI mininstruments, CI minicoagulators (trademark) can be used to promptly control bleeding. Further, CI suction devices are available for aspiration of pleural fluid. Other solutions can also be provided through one of the working miniports of the minithoracoscope and suctioned out after they are utilized. For example, a saline irrigation solution can be introduced to prevent clots. Electrolytic solutions, cooling fluids, cryogenic fluids, chemotherapeutic agents, medicaments, gene therapy agents, contrast agents, and infusion media may also be used. (See U.S. Pat. No. 6,770,070 assigned to R. ITA Medical Systems, Inc. at col. 10, lines 14-17.) Cooling fluids may be provided to ensure the temperatures of energy transfer elements (on sealing and separating instruments) stay within a safe range. Cleaning solutions may be provided to ensure the surface of energy transfer elements stays free of materials such as loose tissue particles or charred tissue.

Step Four: Removal of the Minithoracoscope and Optional Insertion of CI Kink-less, Non-Buckling Chest Tube, If Necessary Once the internal inspection and sampling procedure is complete, a guide wire is introduced through the working miniport of the minithoracoscope and placed in a desired location. The CI minithoracoscope is then removed.

In many cases, once the CI minithoracoscope is removed, the procedure is complete and a chest tube need not be provided. For example, when the CI mininstruments used to obtain biopsy samples seal the site from which the sample is collected (prior to, simultaneously with, or shortly after separating the desired sample from the surrounding tissue), internal bleeding and drainage can be entirely avoided or at least substantially reduced. Use of the rapid tissue sealing and separating capabilities of modern technologies (including those that rely upon heat to both seal and separate) coupled with the small scale of the sampling instruments described herein has the advantage of avoiding the need for a chest tube in many cases.

Chest tubes are generally provided to compensate for incomplete sealing at the biopsy site during incision and sampling. Thus, a chest tube permits the drainage of blood, gases, and internal fluids over an extended period of time, as the biopsied site heals.

If a chest tube is found to be necessary, CI minidilators (trademark) are inserted first, along the tract the tube is to follow in order to enlarge the tract. A Seldinger technique can be used to position the chest tube. A single skin stitch can be used to secure the chest tube in position. Alternatively, other methods of securing the chest tube can be used if the stitch needs to be avoided.

Once the chest tube is properly in place within the interior of the patient, it is connected to a chest drainage system and 20 cm of suction is applied. A post-operative chest X-Ray should be obtained in the immediate post-operative period while the chest tube is in place.

Although any chest tube may be used with the methods of this invention, preferably the CI chest tube is used if a chest tube is determined to be necessary. The CI chest tube is highly desirable as compared with conventional chest tubes because, unlike most flexible chest tubes, it does not kink and does not buckle. Unlike most rigid chest tubes, the CI chest tube is not painful.

The CI chest tube comprises a long, hollow, tubular member with an outer core that is softer than the inner core. The softer outer core minimizes a patient's sensation of pain upon contact of the tube's external periphery with the surrounding bodily environment in which the tube is inserted. The more rigid structural integrity of the inner core minimizes the chance that the tube will buckle (blocking flow) upon bending as it is maneuvered internally. Within the walls of the tube's internal lumen is a deployable elastic element that can be activated from a proximal control site to remove kinks as they emerge, if they emerge. The internally deployable elastic element replaces the conventional trocar insertion method for removing tubular kinks.

Step Five: Removal of Optional Chest Tube

Chest tube removal is at the discretion of the pulmonologist. A band-aid may be applied after the chest tube is removed to protect the insertion area.

A minigenerator as described herein could be used to power the instrument used in the above biopsy procedure.

The present invention is not limited to the embodiments described above. Various changes and modifications can, of course, be made, without departing from the scope and spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A generator for powering a medical device, comprising:
a battery;
an energy converter coupled to the battery;
a monitor circuit;
a controller; and
a final output circuit having a first input and second input, and an output, the final output circuit including a first transformer and a second transformer, each of the first and second transformers having a first winding and a second winding, the first input coupled to the first winding of the first transformer and the first winding of the second transformer, the second input coupled to the first winding of the first transformer and the second winding of the second transformer, the second winding of the first transformer providing the output, the output being coupled to the medical device,
wherein the monitor circuit is configured to obtain a value of current or power supplied to the final output circuit, the controller being adapted to adjust an amount of energy provided by the energy converter to the final output circuit in response to the obtained value of current or power.

2. The generator of claim 1, wherein the first winding of the first transformer includes a first number of windings and the second winding of the first transformer includes a second number of windings, the second number of windings of the first transformer being greater than the first number of windings of the first transformer.

3. The generator of claim 2, wherein an energy output of the energy converter is constant throughout changes in an energy input to the converter.

4. The generator of claim 1, where the final output circuit further comprises a first field effect transistor and a second field effect transistor, the first input being coupled to the first winding of the second transformer through the first field effect transistor, and the second input being coupled to the second winding of the second transformer through the second field effect transistor.

5. The generator of claim 1, wherein the second transformer is adapted to be a swinging choke transformer.

6. The generator of claim 1, wherein the output provides a radiofrequency signal.

7. The generator of claim 1, wherein the output of the final output circuit provides an output signal, the output signal including a power, the controller being configured to vary the power of the output signal based upon a biological tissue characteristic.

8. The generator of claim 7, wherein the controller is further configured to vary an amount of power supplied by the battery while maintaining a constant value associated with the biological tissue characteristic.

9. The generator of claim 1, wherein the output provides an output signal, the controller being configured to adjust each of a frequency, a pulse width, and an amplitude of the output signal in real time.

10. The generator of claim 1, wherein the controller comprises a timing circuit.

11. The generator of claim 10, wherein the controller has an output signal, the timing circuit of the controller being configured to generate the output signal of the controller, the output signal of the controller having a frequency and a pulse width.

* * * * *